United States Patent [19]

Pelerin

[11] Patent Number: 4,822,910

[45] Date of Patent: Apr. 18, 1989

[54] PROCESS FOR THE PRODUCTION OF SUBSTITUTED BENZOIC ACID ESTERS

[75] Inventor: Gérard Pelerin, Cabris, France

[73] Assignee: Societe Anonyme Roure Bertrand Dupont, Argenteuil, France

[21] Appl. No.: 80,798

[22] Filed: Aug. 3, 1987

[30] Foreign Application Priority Data

Aug. 20, 1986 [EP] European Pat. Off. ........ 86.111536.8

[51] Int. Cl.$^4$ ............................................. C07C 69/74
[52] U.S. Cl. ................................................... 560/126
[58] Field of Search ......................................... 560/126

[56] References Cited

PUBLICATIONS

Light, K. et al., CA84(7) 43551g, 1974.

Primary Examiner—Paul J. Killos
Attorney, Agent, or Firm—Wallenstein, Wagner, Hattis & Strampel, Ltd.

[57] ABSTRACT

A process for the production of esters of the general formula

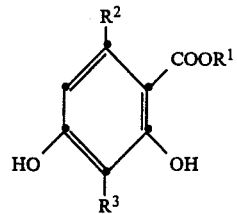

in which $R^1$ signifies methyl or ethyl and $R^2$ and $R^3$, independently from one another, signify $C_{1-4}$-alkyl, is described.

The process is characterized in subjecting a diketo ester of the formula

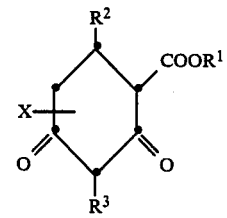

in which $R^1$ to $R^3$ have the above significances; and X is chlorine or bromine, preferably chlorine, and to a dehydrohalogenation process.

The compounds I are known odorants.

4 Claims, No Drawings

PROCESS FOR THE PRODUCTION OF SUBSTITUTED BENZOIC ACID ESTERS

The invention concerns a process for the production of esters of the general formula

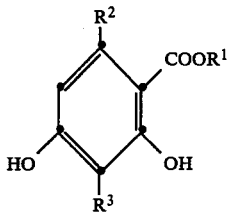

in which $R^1$ signifies methyl or ethyl and $R^2$ and $R^3$, independently from one another, signify $C_{1-4}$-alkyl, many of which esters are known.

Of most interest are the esters I in which $R^1$ signifies methyl or ethyl and $R^2$ and $R^3$ signify methyl.

Especially preferred is the compound with $R^1$, $R^2$ and $R^3$ as methyl.

The compounds I are known odorants, as described in e.g. U.S. Pat. Nos. 3,634,491 and 3,944,596.

The process is characterized in subjecting a diketo ester of the formula

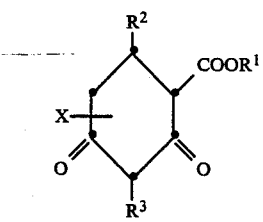

in which $R^1$ to $R^3$ have the above significances; and X is chlorine or bromine, preferably chlorine, and situated in position 1 or 5 to a dehydrohalogenation process.

The dehydrohalogenation process is conveniently brought about by means of a metal halide.

The metal halide can be a chloride, bromide or iodide. A mono- or polyvalent metal cation can function as the counter-ion. Examples of suitable halides are LiCl, NaCl, MgCl$_2$, CaCl$_2$, BaCl$_2$, ZnCl$_2$, SnCl$_4$, LiBr, KI, NaI, etc. The halide can be anhydrous or can contain crystal water.

Preferred are the alkali metal or alkaline earth metal halides, in particular MgCl$_2$, CaCl$_2$, etc.

The ratio of the diketo ester III to the halide is not critical. A ratio of ca. 1:1–1,20 (w/w) is usually convenient, a ratio of ca. 1:1–1,1 is preferred.

The reaction is suitably carried out in the presence of any solvent, whereby those solvents which are marked *, i.e. those with an elevated dielectric constant, e.g. a dielectric constant of about $\geq 30$, e.g. acetonitrile*, formamide, dimethyl formamide*, hexamethyl phosphoric acid triamide*, pyridine, nitrobenzene*, etc. are preferred.

The crude reaction product can be purified by, e.g. recrystallization from a convenient solvent, e.g. toluene, acetonitrile, methanol, ethanol, etc.

Conveniently, the compound of formula III is prepared by reaction of a compound of formula

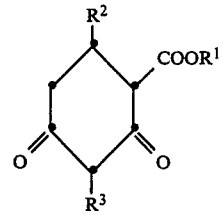

wherein $R^1$ to $R^3$ have the above significances, with a hypohalite, e.g. a hypochlorite or hypobromite, in particular a alkali metal or alkaline earth metal hypohalite. Preferred are NaOCl and Ca(OCl)$_2$, in particular NaOCl, e.g. in the form of Javel water.

The reaction is conveniently carried out in an organic solvent. The nature of this solvent is not critical. Convenient solvents are (chlorinated) hydrocarbons, alcohols, ethers, ketones, nitriles, amides, etc.

Specific examples are: toluene, methylene chloride, dichloro ethane, trichloro ethane, methanol, acetone, acetonitrile, dimethyl formamide, isopropyl ether, etc.

The reaction is carried out in acidic medium, e.g. in a pH range of ca. 1–6, said acidity been brought about by the addition of the respective amount of an acid, preferably, an inorganic acid, e.g. a mineral acid such as sulfuric acid or hydrochloric acid, or an organic acid, e.g. a carboxylic acid such as formic acid, acetic acid, etc.

The process is suitably effected in a temperature range of from approximately 5° to 40° C., preferably at room temperature, i.e. at ca. 20°–25° C.

The working up conveniently consists in a simple decantation step of the organic layer.

If a solvent with an elevated dielectric constant has been used, the resulting solution can be directly used for the dehalogenation step. Otherwise, such solvent is preferably added, whereby even small amounts, even catalytic amounts suffice.

If the compound III is, on the other hand, to be isolated, this can be done by simply distilling off the solvent.

The compounds III are novel and are also part of the invention.

The individual halogenated isomers may be separated by means of column chromatography, e.g. on silica. Said separation is, however, not necessary. The identification can be effected e.g. by NMR.

EXAMPLE 1

To a mixture of 198 g dione ester of formula II with $R^1=R^2=R^3=$ methyl in 580 ml methylene chloride and 280 ml of 30% H$_2$SO$_4$ are added under stirring within 1 hour 670 ml of sodium hypochlorite (150 g/l, ~48° chlorometrically). The temperature is kept at 20° to 25° C. by means of a cold water bath. After the addition, stirring is continued for a further 30 minutes, followed by a decantation step. The organic phase is given into a second reaction vessel, 4 g of anhydrous calcium chloride are added, and 250 ml of methylene chloride are distilled off. At the end of the destillation, the temperature of the vapours is 37° C. and the temperature of the residue is 48° C. 380 ml of acetonitrile are added rapidly, thereupon the distillation is continued until the residue reaches 70° C. There follows a reflux treatment lasting for 10 hours. The calcium chloride is removed by filtration, the mass is transferred to a Vigreux flask and 225 ml of solvent are distilled in vacuo, starting at 400 mm Hg. The crude reaction product is recrystallized in 500 ml of toluene. The yield is 165.5 g (89%) of methyl β-orcine carboxylate.

EXAMPLE 2

198 g of the dione ester of Example 1, 600 ml of trichloroethane, 130 ml of hydrochloric acid (22° B diluted with 130 ml of water) are given to a 2 l reaction flask. 600 ml of the same sodium hypochlorite solution as used in Example 1 are added within 1 hour, the temperature is kept between 20° and 25° C. After the addition, stirring is continued for 15 minutes at the same temperature. The organic phase is decanted and given to a second reaction flask. There are now added 7,6 ml of dimethyl formamide and 7,6 g of $MgCl_2.6H_2O$. The reaction mixture is brought to reflux temperature within 15 minutes and is kept there for 3 hours. The trichloroethane is removed by distillation, this distillation is finalized at a vacuum of 40 mmHg. The yellow residue is dissolved in 560 ml of methanol; the methyl β-orcine carboxylate is precipitated through the addition of 2,8 l water. The reaction product is cooled to 0° to −5° C. and centrifuged. There are obtained 177 g crystals of m.p. 146° C.

EXAMPLE 3

In an analogous manner to the process outlined in Example 1, there was obtained, via the respective intermediate of formula III, the compound I of formula

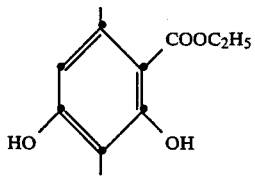

I claim:
1. Compounds of the general formula

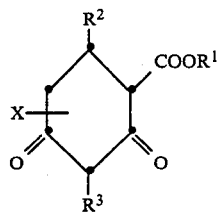

wherein $R^1$ signifies methyl or ethyl and $R^2$ and $R^3$, independently from one another, signify $C_{1-4}$-alkyl; and X is chlorine or bromine, preferably chlorine, and situated in position 1 or 5.

2. Compounds of the general formula III according to claim 1, wherein $R^1=R^2=R^3=$methyl and X is chlorine.

3. A process for the production of compounds of the general formula

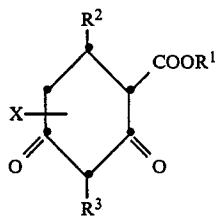

wherein $R^1$ signifies methyl or ethyl and $R^2$ and $R^3$, independently from one another, signify $C_{1-4}$-alkyl; and X is chlorine or bromine, preferably chlorine, and situated in position 1 or 5, which comprises reacting a compound of the formula

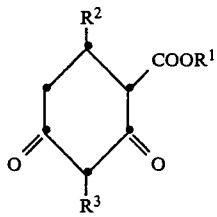

wherein $R^1$ to $R^3$ have the above significance, with a hypohalite.

4. A process according to claim 3, in which $R^1=R^2=R^3=$methyl and X is chlorine.

* * * * *